(12) United States Patent
Acharya et al.

(10) Patent No.: US 12,013,113 B2
(45) Date of Patent: Jun. 18, 2024

(54) DISPLAY SYSTEMS USING IR AND UV TRANSPARENT OPTICAL FILMS

(71) Applicant: 3M INNOVATIVE PROPERTIES COMPANY, St. Paul, MN (US)

(72) Inventors: Bharat R. Acharya, Woodbury, MN (US); Fan Long, Guangzhou (CN); Edward S. Hagermoser, Lancaster, MA (US); Jathan D. Edwards, Afton, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 4 days.

(21) Appl. No.: 18/102,851

(22) Filed: Jan. 30, 2023

(65) Prior Publication Data

US 2023/0250937 A1 Aug. 10, 2023

Related U.S. Application Data

(60) Provisional application No. 63/308,526, filed on Feb. 10, 2022.

(51) Int. Cl.
*A61L 2/10* (2006.01)
*A61L 2/08* (2006.01)
*F21V 9/14* (2006.01)
*G02F 1/1335* (2006.01)
*G02F 1/13357* (2006.01)
*F21Y 113/10* (2016.01)

(52) U.S. Cl.
CPC ............... *F21V 9/14* (2013.01); *A61L 2/085* (2013.01); *A61L 2/10* (2013.01); *G02F 1/133536* (2013.01); *G02F 1/133603* (2013.01); *F21Y 2113/10* (2016.08); *G02F 2203/11* (2013.01)

(58) Field of Classification Search
CPC ......... G02F 1/133536; G02F 1/133603; G09F 9/33; G09G 3/14
See application file for complete search history.

(56) References Cited

U.S. PATENT DOCUMENTS 10,365,768 B2   7/2019  Craven-Bartle et al.
11,360,630 B1 *  6/2022  Li ........................ G06F 3/0412
(Continued)

FOREIGN PATENT DOCUMENTS

TW        I737284   B  *  8/2021
WO   WO-2011071728  A1 *  6/2011 ........... G02B 6/0018

*Primary Examiner* — Mariceli Santiago
(74) *Attorney, Agent, or Firm* — Jonathan L. Tolstedt

(57) ABSTRACT

A display system includes visible light emitting first devices configured to emit a first light having at least a first visible wavelength; ultraviolet light emitting second devices configured to emit a second light having at least a second ultraviolet wavelength; a display panel disposed on the first and second devices; and a reflective polarizer disposed between the display panel and the first and second devices, such that the reflective polarizer has, for the visible wavelength, an average optical reflectance of greater than about 50% when an incident light is polarized along an in-plane first direction and an average optical transmittance of greater than about 50% when the incident light is polarized along an in-plane orthogonal second direction; and an optical transmission of greater than about 30% for the at least the second wavelength and for at least one of the first and second polarization states.

16 Claims, 11 Drawing Sheets

(56) References Cited

U.S. PATENT DOCUMENTS

| | | | |
|---|---|---|---|
| 11,435,618 B2* | 9/2022 | Oh | G02F 1/13334 |
| 2015/0331547 A1 | 11/2015 | Wassvik et al. | |
| 2023/0285609 A1* | 9/2023 | Shiau | A61L 2/24 |

* cited by examiner

Reflective Polarizer (50)

| | Tx(0) | Ty(0) | Ty(60) |
|---|---|---|---|
| 420-680 nm: | 14.91 | 73.96 | 51.08 |

| | Rx(0) | Ry(0) | Ry(60) |
|---|---|---|---|
| 420-680 nm: | 85.09 | 26.04 | 48.92 |

| | Tx(0) | Ty(0) | Ty(60) |
|---|---|---|---|
| 425-680 nm: | 14.35 | 73.93 | 51.16 |

| | Rx(0) | Ry(0) | Ry(60) |
|---|---|---|---|
| 425-680 nm: | 85.65 | 26.07 | 48.84 |

| | Tx(0) | Ty(0) | Ty(60) |
|---|---|---|---|
| 390 nm: | 66.38 | 84.14 | 48.14 |

FIG. 2B

| | xTp0 | yTp0 | xTp60 | yTp60 |
|---|---|---|---|---|
| 425-680 nm: | 0.40 | 0.48 | 0.41 | 0.53 |
| 850-1200 nm: | 84.41 | 85.92 | 60.16 | 97.96 |
| 700-900 nm: | 19.91 | 23.62 | 47.59 | 94.80 |
| 850-1050 nm: | 82.82 | 85.09 | 59.92 | 97.79 |

| | xTp0 | yTp0 | xTp60 | yTp60 |
|---|---|---|---|---|
| 425-680 nm: | 0.58 | 0.43 | 0.46 | 0.22 |
| 850-1200 nm: | 20.56 | 17.65 | 79.50 | 37.96 |
| 700-900 nm: | 0.89 | 0.50 | 2.91 | 0.04 |
| 850-1050 nm: | 1.00 | 0.66 | 66.10 | 22.90 |

Transmission%

|  | OF1 | OF2 | OF3 | Combination (90') |
|---|---|---|---|---|
| 420-680 nm: | 41.82 | 31.31 | 74.07 | 1.13 |
| 390 nm: | 64.54 | 86.59 | 78.49 | 72.19 |

Reflectance %

|  | OF1 | OF2 | OF3 | Combination (90') |
|---|---|---|---|---|
| 420-680 nm: | 58.18 | 68.69 | 25.93 | 98.87 |

Transmittance %

|  | OF1 | OF2 | OF3 | Combination (90') | T2/T1 |
|---|---|---|---|---|---|
| 470 nm: | 0.19 | 85.44 | 87.12 | 0.24 | 459.12 |
| 600 nm: | 86.59 | 0.47 | 84.94 | 0.69 | 181.52 |
| 750 nm: | 83.72 | 78.95 | 0.66 | 0.72 | 119.39 |

FIG. 9C

DISPLAY SYSTEMS USING IR AND UV TRANSPARENT OPTICAL FILMS

SUMMARY

In some aspects of the present description, a display system is provided, the display system including one or more visible light emitting first devices, one or more ultraviolet light emitting second devices, a display panel disposed on the first and second devices, and a reflective polarizer disposed between the display panel and the first and second devices. The one or more visible light emitting first devices are configured to emit a first light having at least a first wavelength in a visible wavelength range extending from about 425 nm to about 680 nm. The one or more ultraviolet light emitting second devices is configured to emit a second light having at least a second wavelength less than about 425 nm. The display panel is configured to receive the emitted first and second lights and form an image. The reflective polarizer is configured such that, for a substantially normally incident light, the reflective polarizer has an average optical reflectance of greater than about 50% for the visible wavelength range when the incident light is polarized along an in-plane first direction and an average optical transmittance of greater than about 50% when the incident light is polarized along an in-plane orthogonal second direction. The reflective polarizer is also configured such that, for the substantially normally incident light, the reflective polarizer has an optical transmission of greater than about 30% for the at least the second wavelength and for at least one of the first and second polarization states.

In some aspects of the present description, a display system is provided, the display system including one or more visible light emitting first devices, a plurality of infrared light emitting second devices, one or more ultraviolet light emitting third devices, one or more infrared light detecting fourth devices, a display panel disposed on the first through fourth devices, a reflective polarizer disposed between the display panel and the first through fourth devices, and an optically reflecting first film disposed so that the first and the second devices are on a first side of the first film and the third and the fourth devices are on an opposite second side of the first film. The one or more visible light emitting first devices are configured to emit a first light having at least a first wavelength in a visible wavelength range extending from about 425 nm to about 680 nm. Each of the plurality of infrared light emitting second devices are configured to emit a second light having at least a second wavelength in an infrared wavelength range extending from about 850 nm to about 1050 nm. The one or more ultraviolet light emitting third devices are configured to emit a third light having at least a third wavelength less than about 425 nm. The one or more infrared light detecting fourth devices are configured to detect a fourth light having the at least the second wavelength. The display panel is configured to receive at least the emitted first and third lights and form an image. For a substantially normally incident light, the reflective polarizer has an average optical reflectance for the visible wavelength range of greater than about 50% when the incident light is polarized along an in-plane first direction, and an average optical transmittance of greater than about 50% when the incident light is polarized along an in-plane orthogonal second direction. For the substantially normally incident light, the reflective polarizer also has an optical transmission of greater than about 30% for the at least the third wavelength and for at least one of the first and second polarization state. For each of the incident light polarized along the in-plane first and second directions, the first film has an average optical reflectance of greater than about 60% for the visible wavelength range and an average optical transmittance of greater than about 50% for the infrared wavelength range.

In some aspects of the present description, a display system is provided, the display system including one or more visible light emitting first devices, one or more ultraviolet light emitting second devices, one or more ultraviolet light detecting third devices, a display panel disposed on the first through third devices, a reflective polarizer disposed between the display panel and the first through third devices, and an optical film disposed so that the first and the second devices are on a first side of the optical film and the third devices are on an opposite second side of the optical film. The one or more visible light emitting first devices are configured to emit a first light having at least a first wavelength in a visible wavelength range extending from about 420 nm to about 680 nm. The one or more ultraviolet light emitting second devices are configured to emit a second light having at least a second wavelength less than about 415 nm. The one or more ultraviolet light detecting third devices are configured to detect a third light having the at least the second wavelength. The display panel is configured to receive at least the emitted first and second lights and form an image. For a substantially normally incident light, the reflective polarizer has an average optical reflectance for the visible wavelength range of greater than about 50% when the incident light is polarized along an in-plane first direction and an average optical transmittance greater than about 50% when the incident light is polarized along an in-plane orthogonal second direction. For the substantially normally incident light, the reflective polarizer also has an optical transmission of greater than about 30% for the at least the second wavelength and for at least one of the first and second polarization states. For each of the incident light polarized along the in-plane first and second directions, the optical film has an average optical reflectance of greater than about 60% for the visible wavelength range and an optical transmittance of greater than about 50% for the at least the second wavelength.

In some aspects of the present description, a display system is provided, the display system including one or more visible light emitting first devices, one or more infrared light emitting second devices, one or more infrared light detecting third devices, a display panel disposed on the first through third devices, a reflective polarizer disposed between the display panel and the first through third devices, an optical film disposed so that the first and the second devices are on a first side of the optical film and the third devices are on an opposite second side of the optical film. The one or more visible light emitting first devices are configured to emit a first light having at least a first wavelength in a visible wavelength range extending from about 420 nm to about 680 nm. The one or more infrared light emitting second devices are configured to emit a second light having at least a second wavelength in an infrared wavelength range extending from about 850 nm to about 1050 nm. The one or more infrared light detecting third devices are configured to detect a third light having the at least the second wavelength. For a substantially normally incident light, the reflective polarizer has an average optical reflectance for the visible wavelength range of greater than about 50% when the incident light is polarized along an in-plane first direction, and an average optical transmittance of greater than about 50% when the incident light is polarized along an in-plane orthogonal second direction. For the substantially normally incident light, the reflective polarizer also has an optical transmission of greater than about 30% for the at least the second wavelength and for at least one of the first and second polarization states. For each of the incident light polarized along the in-plane first and second directions, the optical film has an average optical reflectance of greater than about 60% for the visible wavelength range and an optical transmittance of greater than about 50% for the at least the second wavelength. The optical film includes first, second, and third optical films. Each of the first, second and third optical films include a plurality of polymeric layers numbering at least 10 in total, and each of the polymeric layers has an average thickness of less than about 500 nm. For a substantially normally incident light, three spaced apart wavelengths in a reflection wavelength range extending from about 450 nm to about 800 nm, and for each of the incident light polarized along the in-plane first and second directions, each of the first, second and third optical films has an optical transmittance of greater than about 50% for the at least the second wavelength, and each of the first, second and third optical films also has an optical transmittance T1 for one of the three spaced apart wavelengths and an optical transmittance T2 for each of the other two of the three spaced apart wavelengths, such that the ratio T2/T1 is greater than or equal to about 10.

BRIEF DESCRIPTION OF THE DRAWINGS

FIG. 2B is a table summarizing the transmission and reflection percentages by wavelength range for a reflective polarizer in a display system, in accordance with an embodiment of the present description;

FIGS. 9A-9C is a chart showing the transmission percentage versus wavelength for an optical film in a display system, in accordance with an embodiment of the present description.

DETAILED DESCRIPTION

Figure 1:
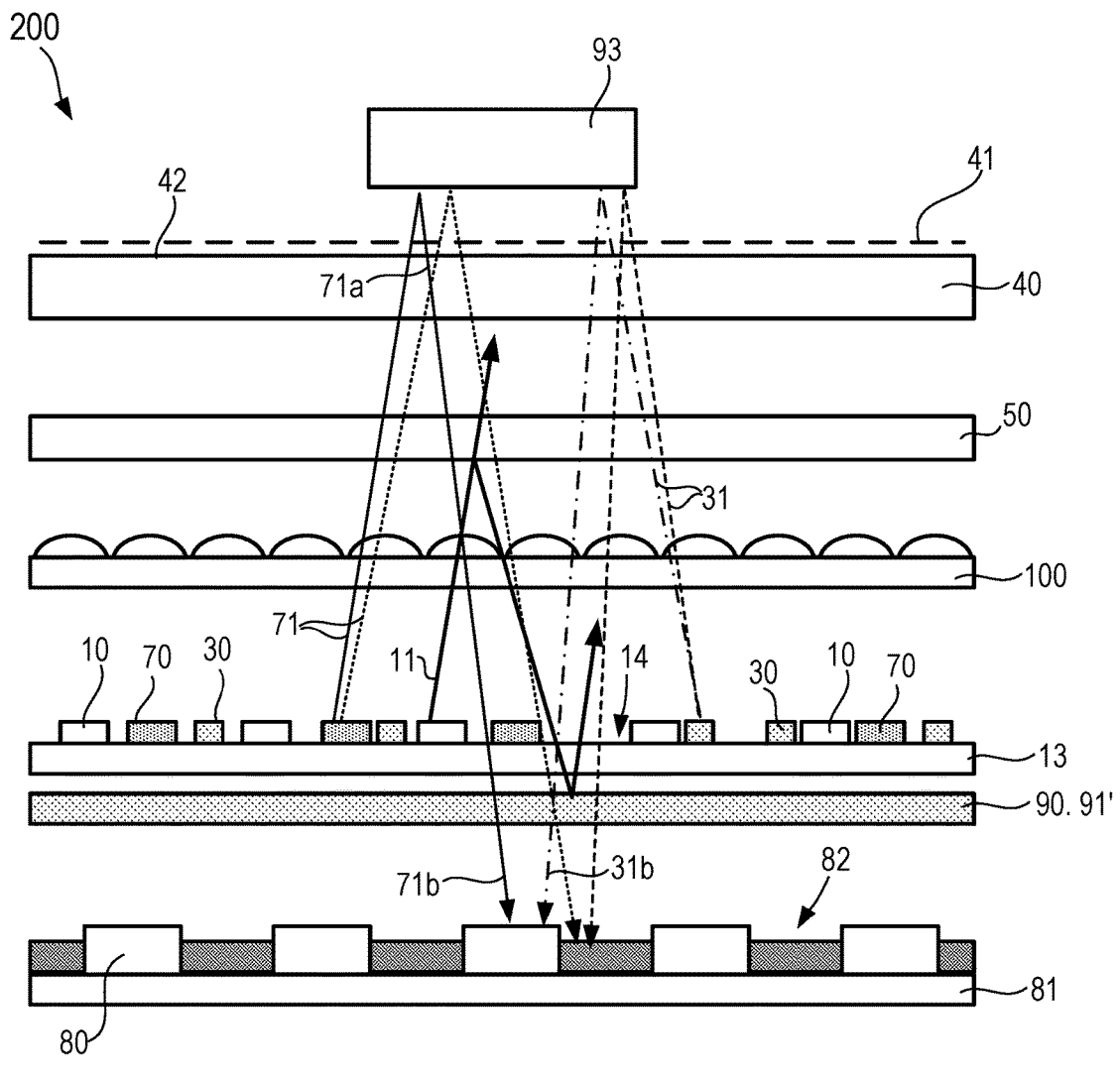
FIG. 1 is a side view of a display system with visible, infrared, and ultraviolet light emitting devices, in accordance with an embodiment of the present description.

In the following description, reference is made to the accompanying drawings that form a part hereof and in which various embodiments are shown by way of illustration. The drawings are not necessarily to scale. It is to be understood that other embodiments are contemplated and may be made without departing from the scope or spirit of the present description. The following detailed description, therefore, is not to be taken in a limiting sense.

To provide touch functionality in large area displays, different touch technologies have been utilized in the art. Among these, one technology uses an array of infrared light sources (e.g., LEDs) and infrared light photodetectors (sensors) mounted around the edge of the touch screen placed over the display panel so that the light is injected into it using total internal reflection. In some cases, an array of photodetectors may be positioned on the opposite side of the touch screen to receive the signal from the infrared light sources. When an object (e.g., finger or stylus) touches the screen, the intensity of infrared light at the photodetectors is reduced and the location of the object may be determined using a triangulation algorithm based on the relative distribution of infrared intensity at individual photodiodes. While this principle works very well for relatively small screens, it can become exponentially expensive with larger display panels due to the high cost associated with obtaining high quality (e.g., display uniformity, optical quality, flatness, etc.) needed for signal propagation across large area using total internal reflection. Also, the efficient in-coupling and out-coupling of infrared light to the touch panel while maintaining a thin profile, eliminating interference from ambient light, and preventing surface contamination pose additional challenges.

According to some aspects of the present description, a display system which allows the transmission of infrared light (e.g., near infrared light) throughout the entire LCD enables the use of infrared LEDs and sensors directly behind and beneath the display panel. In other aspects of the present description, the display system utilizes an optical film technology that is transparent to both ultraviolet and infrared light, providing an opportunity to use both ultraviolet and infrared light sources behind displays to enable touch function and potentially disinfecting the displays when not in use.

According to some aspects of the present description, a display system includes one or more visible (human-visible) light emitting first devices, one or more ultraviolet light emitting second devices, a display panel disposed on the first and second devices, and a reflective polarizer disposed between the display panel and the first and second devices. In some embodiments, the one or more visible light emitting first devices may be configured to emit a first light having at least a first wavelength in a visible wavelength range extending from about 425 nm to about 680 nm. In some embodiments, the one or more ultraviolet light emitting second devices may be configured to emit a second light having at least a second wavelength less than about 425 nm, or less than about 420 nm, or less than about 415 nm, or less than about 410 nm, or less than about 405 nm, or less than about 400 nm, or less than about 395 nm. In some embodiments, the display panel may be configured to receive the emitted first and second lights and form an image for viewing by a user. In some embodiments, the second light (i.e., the ultraviolet light) may be configured to reach and disinfect at least an exposed front surface of the display system.

In some embodiments, the pluralities of the first and second devices may be disposed on a same common first substrate. In some embodiments, at least in regions of the common first substrate between the first and second devices and for a substantially normally incident light and for each of the first and second polarization states, the first substrate may have an optical transmittance of greater than about 60%, or greater than about 70%, or greater than about 80%, or greater than about 90% for the at least the first wavelength.

In some embodiments, the reflective polarizer may be configured such that, for a substantially normally incident light, the reflective polarizer has an average optical reflectance of greater than about 50%, or 55%, or 60%, or 70%, or 75%, or 80%, or 85%, or 90% for the visible wavelength range when the incident light is polarized along an in-plane first direction (e.g., polarized along an x-axis of the reflective polarizer) and an average optical transmittance of greater than about 50%, or 55%, or 60%, or 65%, or 70%, or 75% when the incident light is polarized along an in-plane orthogonal second direction (e.g., the y-axis of the reflective polarizer). In some embodiments, the reflective polarizer may also be configured such that, for the substantially normally incident light, the reflective polarizer has an optical transmission of greater than about 30%, or 35%, or 40%, or 45%, or 50%, or 55%, or 60%, or 65%, or 70%, or 75%, or 80% for the at least the second wavelength and for at least one of the first and second polarization states.

In some embodiments, the display system may further include a plurality of infrared light emitting third devices, a plurality of infrared light detecting fourth devices, and an optically reflecting first film disposed between the third and the fourth devices. In some embodiments, each of the plurality of infrared light emitting third devices may be configured to emit a third light having at least a third wavelength in an infrared wavelength range extending from about 850 nm to about 1050 nm. In some embodiments, each of the plurality of infrared light detecting fourth devices may be configured to detect a fourth light having the at least the third wavelength.

In such embodiments, for a substantially normally incident light and for each of the incident light polarized along the in-plane first and second directions, the first film may have an average optical reflectance of greater than about 60%, or greater than about 70%, or greater than about 80%, or greater than about 90%, or greater than about 95%, or greater than about 98% for the visible wavelength range, and may have an average optical transmittance of greater than about 50%, or greater than about 55%, or greater than about 60%, or greater than about 65%, or greater than about 70%, or greater than about 75%, or greater than about 80% for the infrared wavelength range.

In such embodiments, the pluralities of the first, second, and third devices may be disposed on a same common first substrate. In some such embodiments, at least in regions between the first, second, and third devices and for a substantially normally incident light and for each of the first and second polarization states, the first substrate may have an optical transmittance of greater than about 60%, or greater than about 70%, or greater than about 80%, or greater than about 90% for each of the at least the first and the third wavelengths. In such embodiments, the fourth devices may be disposed on a same common second substrate, and wherein at least in regions between the fourth devices and for a substantially normally incident light and for each of the first and second polarization states, the second substrate may have an optical absorption of greater than about 60%, or greater than about 70%, or greater than about 80%, or greater than about 90% at the at least the third wavelength.

In such embodiments, the display system may be configured so that an object (e.g., a finger or stylus) disposed proximate the display system reflects at least a portions of the third light toward the fourth devices as a third reflected light. In such embodiments, the first film may be configured to transmit at least 30%, or at least 35%, or at least 40%, or at least 45%, or at least 50% of the third reflected light as a third transmitted light, and each of at least three of the fourth devices may be configured to receive and detect at least 5%, or at least 6%, or at least 7%, or at least 8%, or at least 9%, or at least 10%, or at least 15%, or at least 20% of the third transmitted light. In some embodiments, the detection of the third transmitted light by the at least three of the fourth devices may, in combination, allow a detection of a location of the object.

In some embodiments, the display system may further include an optical diffuser disposed between the reflective polarizer and the second devices. In such embodiments, the optical diffuser may be configured to diffuse the second light emitted by the one or more ultraviolet light emitting second devices.

According to some aspects of the present description, a display system includes one or more visible light emitting first devices, a plurality of infrared light emitting second devices, one or more ultraviolet light emitting third devices, one or more infrared light detecting fourth devices, a display panel disposed on the first through fourth devices, a reflective polarizer disposed between the display panel and the first through fourth devices, and an optically reflecting first film disposed so that the first and the second devices are on a first side of the first film and the third and the fourth devices are on an opposite second side of the first film.

In some embodiments, the one or more visible light emitting first devices may be configured to emit a first light having at least a first wavelength in a visible wavelength range extending from about 425 nm to about 680 nm. In some embodiments, each of the plurality of infrared light emitting second devices may be configured to emit a second light having at least a second wavelength in an infrared wavelength range extending from about 850 nm to about 1050 nm. In some embodiments, the one or more ultraviolet light emitting third devices may be configured to emit a third light having at least a third wavelength less than about 425 nm, or less than about 420 nm, or less than about 415 nm, or less than about 410 nm, or less than about 405 nm, or less than about 400 nm, or less than about 395 nm.

In some embodiments, the one or more infrared light detecting fourth devices may be configured to detect a fourth light having the at least the second wavelength. In some embodiments, the display panel may be configured to receive at least the emitted first and third lights and form an image for viewing by a user.

In some embodiments, for a substantially normally incident light, the reflective polarizer may have an average optical reflectance for the visible wavelength range of greater than about 50%, or greater than about 55%, or greater than about 60%, or greater than about 70%, or greater than about 75%, or greater than about 80%, or greater than about 85%, or greater than about 90% when the incident light is polarized along an in-plane first direction, and may have an average optical transmittance of greater than about 50%, or greater than about 55%, or greater than about 60%, or greater than about 65%, or greater than about 70%, or greater than about 75% when the incident light is polarized along an in-plane orthogonal second direction.

In some embodiments, for the substantially normally incident light, the reflective polarizer may also have an optical transmission of greater than about 30%, or greater than about 35%, or greater than about 40%, or greater than about 45%, or greater than about 50%, or greater than about 55%, or greater than about 60%, or greater than about 65%, or greater than about 70%, or greater than about 75%, or greater than about 80% for the at least the third wavelength and for at least one of the first and second polarization state. In some embodiments, for each of the incident light polarized along the in-plane first and second directions, the first film may have an average optical reflectance of greater than about 60%, or greater than about 70%, or greater than about 80%, or greater than about 90%, or greater than about 95%, or greater than about 98% for the visible wavelength range and may have an average optical transmittance of greater than about 50%, or greater than about 55%, or greater than about 60%, or greater than about 65%, or greater than about 70%, or greater than about 75%, or greater than about 80% for the infrared wavelength range.

In some embodiments, the display system may be configured so that an object (e.g., a finger or a stylus) disposed proximate the display system reflects at least a portions of the second light toward the fourth devices as a second reflected light. In such embodiments, the first film may be configured to transmit at least 30%, or at least 35%, or at least 40%, or at least 45%, or at least 50% of the second reflected light as a second transmitted light. In such embodiments, each of at least three of the fourth devices may be configured to receive and detect at least 5%, or at least 6%, or at least 7%, or at least 8%, or at least 9%, or at least 10%, or at least 15%, or at least 20% of the second transmitted light. In such embodiments, the detection by the at least three of the fourth devices, in combination, may allow a detection of a location of the object.

In some embodiments, for the substantially normally incident light and for each of the incident light polarized along the in-plane first and second directions, the first film may have an optical transmission of greater than about 30%, or greater than about 35%, or greater than about 40%, or greater than about 45%, or greater than about 50%, or greater than about 55%, or greater than about 60%, or greater than about 65%, or greater than about 70%, or greater than about 75%, or greater than about 80%, or greater than about 85% for the at least the third wavelength. In some embodiments, the fourth light (i.e., ultraviolet light) may be configured to reach and disinfect at least an exposed front surface of the display system.

According to some aspects of the present description, display system includes one or more visible light emitting first devices, one or more ultraviolet light emitting second devices, one or more ultraviolet light detecting third devices, a display panel disposed on the first through third devices, a reflective polarizer disposed between the display panel and the first through third devices, and an optical film disposed so that the first and the second devices are on a first side of the optical film and the third devices are on an opposite second side of the optical film. In some embodiments, the one or more visible light emitting first devices may be configured to emit a first light having at least a first wavelength in a visible wavelength range extending from about 420 nm to about 680 nm. In some embodiments, the one or more ultraviolet light emitting second devices may be configured to emit a second light having at least a second wavelength less than about 415 nm, or less than about 410 nm, or less than about 405 nm, or less than about 400 nm, or less than about 395 nm. In some embodiments, the one or more ultraviolet light detecting third devices may be configured to detect a third light having the at least the second wavelength. In some embodiments, the display panel may be configured to receive at least the emitted first and second lights and form an image for viewing by a user. In some embodiments, the third light may be configured to reach and disinfect at least an exposed front surface of the display system.

In some embodiments, for a substantially normally incident light, the reflective polarizer may have an average optical reflectance for the visible wavelength range of greater than about 50%, or greater than about 55%, or greater than about 60%, or greater than about 70%, or greater than about 75%, or greater than about 80%, or greater than about 85%, or greater than about 90% when the incident light is polarized along an in-plane first direction (e.g., the x-axis), and may have an average optical transmittance greater than about 50%, or greater than about 55%, or greater than about 60%, or greater than about 65%, or greater than about 70%, or greater than about 75% when the incident light is polarized along an in-plane orthogonal second direction (e.g., the y-axis). In some embodiments, for the substantially normally incident light, the reflective polarizer may also have an optical transmission of greater than about 30%, or greater than about 35%, or greater than about 40%, or greater than about 45%, or greater than about 50%, or greater than about 55%, or greater than about 60%, or greater than about 65%, or greater than about 70%, or greater than about 75%, or greater than about 80% for the at least the second wavelength and for at least one of the first and second polarization states. In some embodiments, for each of the incident light polarized along the in-plane first and second directions, the optical film may have an average optical reflectance of greater than about 60%, or greater than about 65%, or greater than about 70%, or greater than about 75%, or greater than about 80%, or greater than about 85%, or greater than about 90%, or greater than about 95%, or greater than about 98% for the visible wavelength range and may have an optical transmittance of greater than about 50%, or greater than about 55%, or greater than about 60%, or greater than about 65%, or greater than about 70% for the at least the second wavelength.

In some embodiments, the optical film may include first, second, and third optical films, and each of the first, second and third optical films may have a plurality of polymeric layers numbering at least 10, or at least 50, or at least 100, or at least 150, or at least 200, or at least 250, or at least 300 in total. In such embodiments, each of the polymeric layers may have an average thickness of less than about 500 nm, or less than about 450 nm, or less than about 400 nm, or less than about 350 nm, or less than about 300 nm, or less than about 250 nm, or less than about 200 nm. In such embodiments, for a substantially normally incident light, three spaced apart wavelengths in a reflection wavelength range extending from about 450 nm to about 800 nm, and for each of the incident light polarized along the in-plane first and second directions, each of the first, second, and third optical films may have an optical transmittance of greater than about 50%, or greater than about 55%, or greater than about 60%, or greater than about 65%, or greater than about 70% for the at least the second wavelength. In such embodiments, each of the first, second, and third optical films may have an optical transmittance T1 for one of the three spaced apart wavelengths and an optical transmittance T2 for each of the other two of the three spaced apart wavelengths, such that the ratio T2/T1 is greater than or equal to about 10, or about 20, or about 50, or about 75, or about 100, or about 150, or about 200, or about 250, or about 300, or about 350, or about 400, or about 450. In some such embodiments, the first, second, and third optical films may be bonded to each other via first and second adhesive layers.

According to some aspects of the present description, a display system includes one or more visible light emitting first devices, one or more infrared light emitting second devices, one or more infrared light detecting third devices, a display panel disposed on the first through third devices, a reflective polarizer disposed between the display panel and the first through third devices, an optical film disposed so that the first and the second devices are on a first side of the optical film and the third devices are on an opposite second side of the optical film.

In some embodiments, the one or more visible light emitting first devices may be configured to emit a first light having at least a first wavelength in a visible wavelength range extending from about 420 nm to about 680 nm. In some embodiments, the one or more infrared light emitting second devices may be configured to emit a second light having at least a second wavelength in an infrared wavelength range extending from about 850 nm to about 1050 nm. In some embodiments, the one or more infrared light detecting third devices may be configured to detect a third light having the at least the second wavelength.

In some embodiments, for a substantially normally incident light, the reflective polarizer may have an average optical reflectance for the visible wavelength range of greater than about 50%, or greater than about 55%, or greater than about 60%, or greater than about 70%, or greater than about 75%, or greater than about 80%, or greater than about 85%, or greater than about 90% when the incident light is polarized along an in-plane first direction, and an average optical transmittance of greater than about 50%, or greater than about 55%, or greater than about 60%, or greater than about 65%, or greater than about 70%, or greater than about 75% when the incident light is polarized along an in-plane orthogonal second direction. For the substantially normally incident light, the reflective polarizer also has an optical transmission of greater than about 30% or greater than about 35%, or greater than about 40%, or greater than about 45%, or greater than about 50%, or greater than about 55%, or greater than about 60%, or greater than about 65%, or greater than about 70%, or greater than about 75%, or greater than about 80% for the at least the second wavelength and for at least one of the first and second polarization states. For each of the incident light polarized along the in-plane first and second directions, the optical film has an average optical reflectance of greater than about 60%, or greater than about 65%, or greater than about 70%, or greater than about 75%, or greater than about 80%, or greater than about 85%, or greater than about 90%, or greater than about 95%, or greater than about 98% for the visible wavelength range and an optical transmittance of greater than about 50%, or greater than about 55%, or greater than about 60%, or greater than about 65%, or greater than about 70%, or greater than about 80%, or greater than about 85% for the at least the second wavelength.

The optical film includes first, second, and third optical films. Each of the first, second and third optical films include a plurality of polymeric layers numbering at least 10, or at least 50, or at least 100, or at least 150, or at least 200, or at least 250, or at least 300 in total, and each of the polymeric layers has an average thickness of less than about 500 nm, or less than about 450 nm, or less than about 400 nm, or less than about 350 nm, or less than about 300 nm, or less than about 250 nm, or less than about 200 nm. For a substantially normally incident light, three spaced apart wavelengths in a reflection wavelength range extending from about 450 nm to about 800 nm, and for each of the incident light polarized along the in-plane first and second directions, each of the first, second and third optical films has an optical transmittance of greater than about 50%, or greater than about 55%, or greater than about 60%, or greater than about 65%, or greater than about 70%, or greater than about 80%, or greater than about 85% for the at least the second wavelength, and each of the first, second and third optical films also has an optical transmittance T1 for one of the three spaced apart wavelengths and an optical transmittance T2 for each of the other two of the three spaced apart wavelengths, such that the ratio T2/T1 is greater than or equal to about 10, or about 20, or about 50, or about 75, or about 100, or about 150, or about 200, or about 250, or about 300, or about 350, or about 400, or about 450. In some embodiments, the first, second, and third optical films may be bonded to each other via first and second adhesive layers.

In some embodiments, the display system may further include one or more ultraviolet light emitting devices configured to emit a fourth light having at least a third wavelength less than about 425, or less than about 420, or less than about 415, or less than about 410, or less than about 405, or less than about 400 nm. In such embodiments, the fourth light may be configured to reach and disinfect at least an exposed front surface of the display system.

Figure 2A:
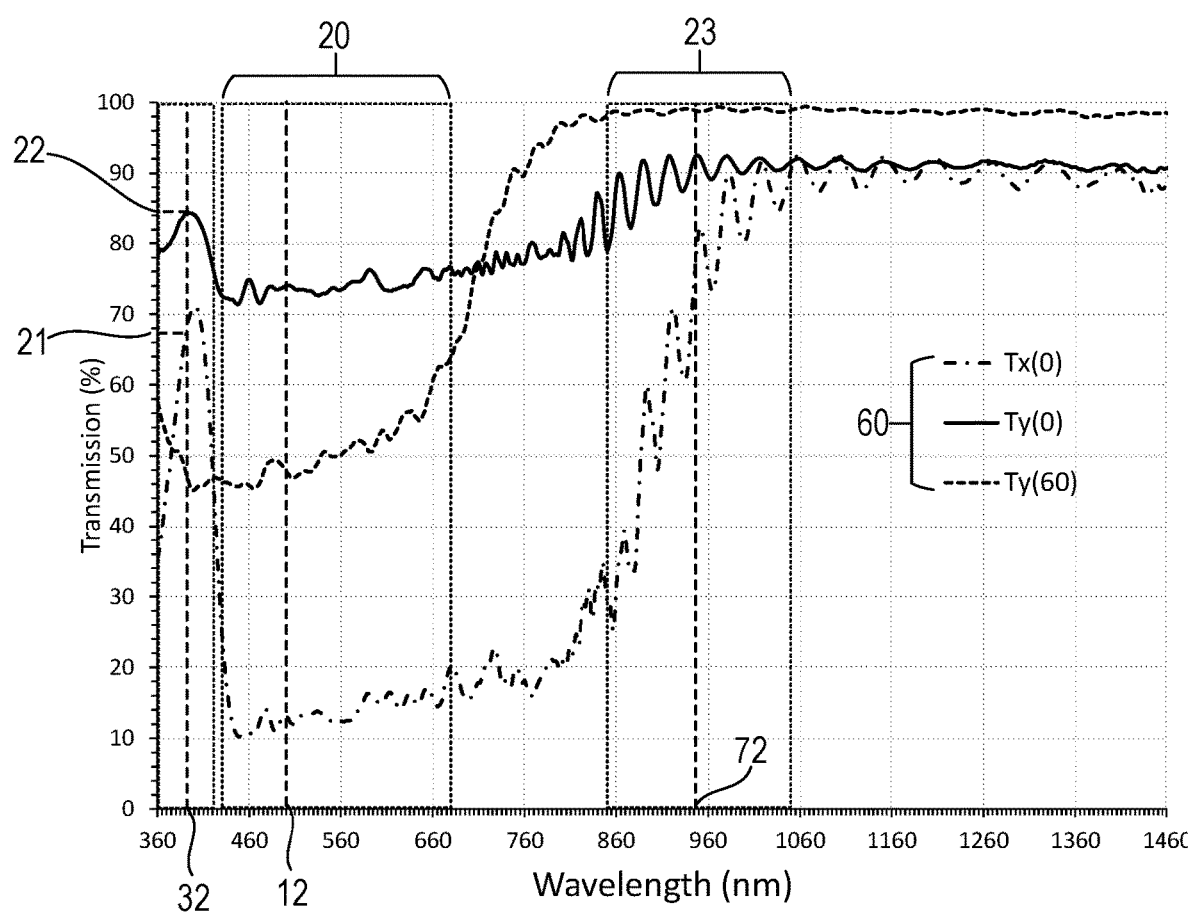
FIG. 2A is a chart showing the transmission percentage versus wavelength for a reflective polarizer in a display system, in accordance with an embodiment of the present description.

Turning now to the figures, FIG. 1 is a side view of a display system with visible, infrared, and ultraviolet light emitting devices, according to the present description. In the discussion of FIG. 1, references may be made to the chart and table of FIGS. 2A and 2B, and FIGS. 1, 2A, and 2B are best reviewed together for the following discussion.

In some embodiments, display system 200 includes one or more visible light emitting first devices 10, and one or more ultraviolet light emitting second devices 30. In some embodiments, display system 200 further includes one or more infrared light emitting third devices 70. In some embodiments, the one or more visible light emitting first devices may be configured to emit a first light 11 having at least a first wavelength 12 in a visible wavelength range 20 (refer also to FIG. 2A) extending from about 425 nm to about 680 nm. In some embodiments, display system 200 may further include a one or more infrared light detecting fourth devices 80 configured to detect a fourth light 71b having the at least the third wavelength 72.

In some embodiments, the one or more ultraviolet light emitting second devices 30 may be configured to emit a second light 31 having at least a second wavelength 32 less than about 425 nm (or less than about 420 nm, or less than about 415 nm, or less than about 410 nm, or less than about 405 nm, or less than about 400 nm (again refer to FIG. 2A, wavelength 32). In some embodiments, the one or more infrared light emitting third devices 70 may be configured to emit a third light 71 having at least a third wavelength 72 in an infrared wavelength range 23 extending from about 850 nm to about 1050 nm (see FIG. 2A for wavelength 72 and infrared wavelength range 23).

In some embodiments, each of the first 10, second 30, and third 70 devices may be disposed on a same common first substrate 13. In some embodiments, common first substrate 13, at least in regions 14 between the first 10, second 30, and third 70 devices, and for a substantially normally incident light and for each of the first and second polarization states, the first substrate 13 may have an optical transmittance of greater than about 60%, or greater than about 70%, or greater than about 80%, or greater than about 90% for each of the at least the first wavelength 12 (i.e., the visible wavelength) and the third wavelength 72 (i.e., the infrared wavelength).

In some embodiments, the one or more fourth devices may be disposed on a same common second substrate 81. In some embodiments, at least in regions 82 between the fourth devices 80 and for a substantially normally incident light and for each of the first and second polarization states, the second substrate may have an optical absorption of greater than about 60%, or greater than about 70%, or greater than about 80%, or greater than about 90% at the at least the third wavelength 72 (see, e.g., the optical transmission curves provided for second substrate 81 in FIGS. 5A-5B). In some embodiments, display system 200 further includes a display panel 40 disposed on the first 10 and second 30 devices and configured to receive the emitted first light 11 and emitted second light 31 and form an image 41 (for viewing by a user, not shown).

In some embodiments, display system 200 further includes a reflective polarizer 50 disposed between display panel 40 and the first 10 and second 30 devices. In some embodiments, for a substantially normally incident light (e.g., normally incident light 60 of FIG. 3), reflective polarizer 50 may have an average optical reflectance (see, e.g., the value for Rx(0) for the visible wavelength range extending from 425 nm to 680 nm, FIG. 2B) for the visible wavelength range of greater than about 50%, or greater than 55%, or greater than 60%, or greater than 70%, or greater than 75%, or greater than 80%, or greater than 85%, or greater than 90% (e.g., 85.65%, as shown in FIG. 2B) when the incident light is polarized along an in-plane first direction (e.g., along the x-axis). In some embodiments, for the substantially normally incident light, reflective polarizer 50 may have an average optical transmittance (see Ty(0), FIG. 2B, 425-680 nm) of greater than about 50%, or greater than about 55%, or greater than about 60%, or greater than about 65%, or greater than about 70%, or greater than about 75% (e.g., 73.93% as shown in FIG. 2B) when the incident light is polarized along an in-plane orthogonal second direction (e.g., along the y-axis of reflective polarizer 50. In some embodiments, for the substantially normally incident light, reflective polarizer 50 may have an optical transmission (e.g., see transmission levels 21, 22, FIG. 2A) of greater than about 30%, or greater than about 35%, or greater than about 40%, or greater than about 45%, or greater than about 50%, or greater than about 55%, or greater than about 60%, or greater than about 65%, or greater than about 70%, or greater than about 75%, or greater than about 80% for the at least the second wavelength 32 and for at least one of the first and second polarization states (e.g., level 21 is 66.38% and level 22 is 84.14%, for a second wavelength 32 equal to about 390 nm).

In some embodiments, display system 200 may further include an optically reflecting first film 90 disposed between the third 70 and the fourth 80 devices. In some embodiments, for a substantially normally incident light 61 (e.g., normally incident light 61 of FIG. 3), and for each of the incident light 61 polarized along the in-plane first and second directions, the first film 90 may have an average optical reflectance of greater than about 60%, or greater than about 70%, or greater than about 80%, or greater than about 90%, or greater than about 95%, or greater than about 98% for the visible wavelength range 20 and an average optical transmittance of greater than about 50%, or greater than about 55%, or greater than about 60%, or greater than about 65%, or greater than about 70%, or greater than about 75%, or greater than about 80%) for the infrared wavelength range 23 (see, e.g., the optical transmission curves and wavelength ranges provided for first film 90 in FIGS. 4A-4B). (Note: Optical film 90' shown in FIG. 1 is another embodiment of optical film 90 and will be discussed in additional detail elsewhere herein. Either embodiment 90 or 90' may be used in the embodiment of FIG. 1.)

In some embodiments, display system 200 may be configured such that and object 93 (e.g., a finger or a stylus) proximate an exposed front surface 42 of display system 200 reflects at least a portion of the third light 71 toward the fourth devices 80 as a third reflected light 71a. In some embodiments, first film 90 may be configured to transmit at least 30%, or at least 35%, or at least 40%, or at least 45%, or at least 50% of the third reflected light 71a as a third transmitted light 71b. In some embodiments, each of at least three of the fourth devices 80 may be configured to receive and detect at least 5%, or at least 6%, or at least 7%, or at least 8%, or at least 9%, or at least 10%, or at least 15%, or at least 20% of the third transmitted light 71b. In some embodiments, the detection by the at least three of the fourth devices 80, in combination, may allow a detection of a location of object 93 relative to exposed front surface 42. In some embodiments, second light 31 (e.g., containing ultraviolet wavelengths) may be configured to reach and disinfect at least exposed front surface 42 of display system 200. In some embodiments, at least a portion of second light 31 is reflected by object 93 as second reflected light 31b and may substantially be transmitted back through display system 200.

In some embodiments, display system may further include an optical diffuser 100 disposed between the reflective polarizer 50 and the second devices 30. In some embodiments, optical diffuser 100 may be configured to diffuse second light 31 emitted by the one or more ultraviolet light emitting second devices 30.

FIG. 2A is a chart showing the transmission percentage versus wavelength for a reflective polarizer in a display system, such as reflective polarizer 50 from FIG. 1. FIG. 2B is a table summarizing the transmission and reflection percentages by wavelength range by an embodiment of reflective polarizer 50, and the data in FIG. 2B can be derived from the graph of FIG. 2A. The three plotlines on FIG. 2A represent a plot of transmission percentage of an incident light 60 at an incidence angle of 0 degrees (substantially normal to reflective polarizer 50) and an incidence angle of 60 degrees. For example, plot Tx(0) represents the transmission percentage of light polarized to the x-axis (e.g., polarized to a first direction) of reflective polarizer 50 and having an angle of incidence that is about 0 degrees. Plot Ty(0) represents the transmission percentage of light polarized to the y-axis (e.g., polarized to a second direction, substantially orthogonal to the first direction) of reflective polarizer 50 and having an angle of incidence that is about 0 degrees. Plot Ty(60) represents the transmission percentage of light polarized to the y-axis of reflective polarizer 50 and having an angle of incidence that is about 60 degrees. These plotlines are shown for wavelengths of light in a range extending from about 420 nm to about 1400 nm, including a human-visible wavelength range 20 (with a first representative wavelength 12) extending from about 420 nm to 680 nm, an infrared wavelength range 23 (with a second representative wavelength 72) extending from about 850 nm to about 1050 nm, and an ultraviolet wavelength range with wavelengths typically less than about 415 nm, including third representative wavelength 32.

FIG. 2B provides tables summarizing the transmission percentages for each of the three plotlines of FIG. 2A across the visible wavelength range 20, showing average transmission percentages (Tx(0), Ty(0), and Ty(60)) for wavelengths from 420 nm to 680 nm and from 425 nm to 680 nm, and average reflectance percentages (Rx(0), Ry(0), and Ry(60)) for the same wavelengths. Also shown are the transmission percentages for the three plotlines of FIG. 2A for third wavelength 32 (an ultraviolet wavelength, 390 nm).

Figure 3:
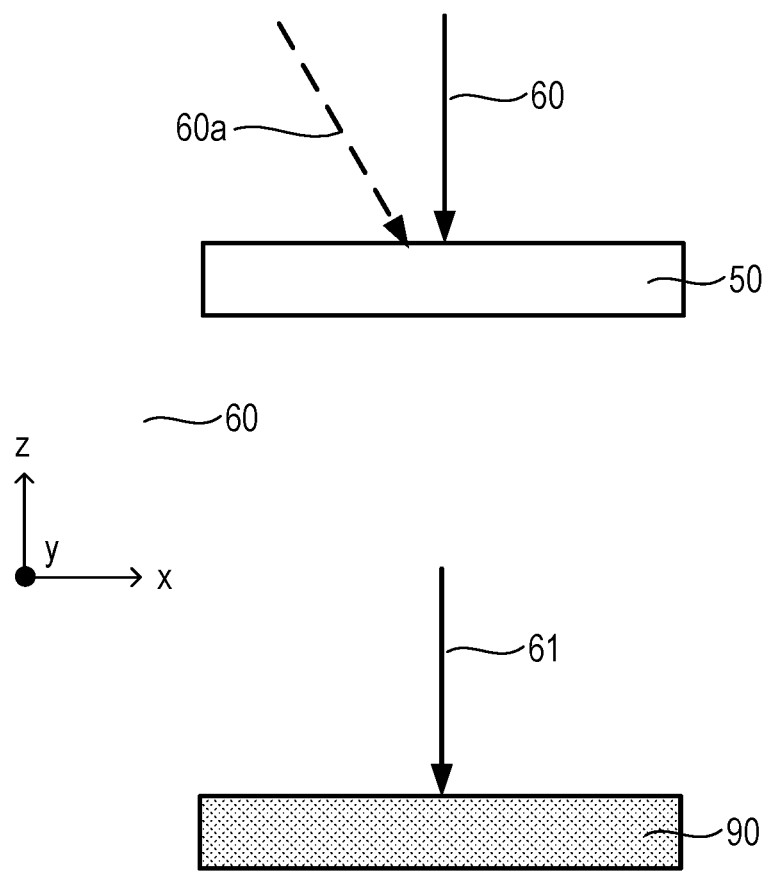
FIG. 3 is an illustration of normally incident light on optical films, in accordance with an embodiment of the present description.

FIG. 3 is an illustration of normally incident light on optical films, such as reflective polarizer 50 and optically reflecting first film 90, as shown in FIG. 1. Incident light 60 is shown in FIG. 3 at an incidence angle that is substantially 0 degrees, or substantially perpendicular (orthogonal) to reflective polarizer 50. Similarly, incident light 61 is shown in FIG. 3 at an incidence angle that is also substantially 0 degrees, or substantially perpendicular (orthogonal) to first film 90. For comparison, incident light 60a is shown at an incident angle that is substantially 60 degrees (dashed arrow of FIG. 3).

Figures 4A, 4B:
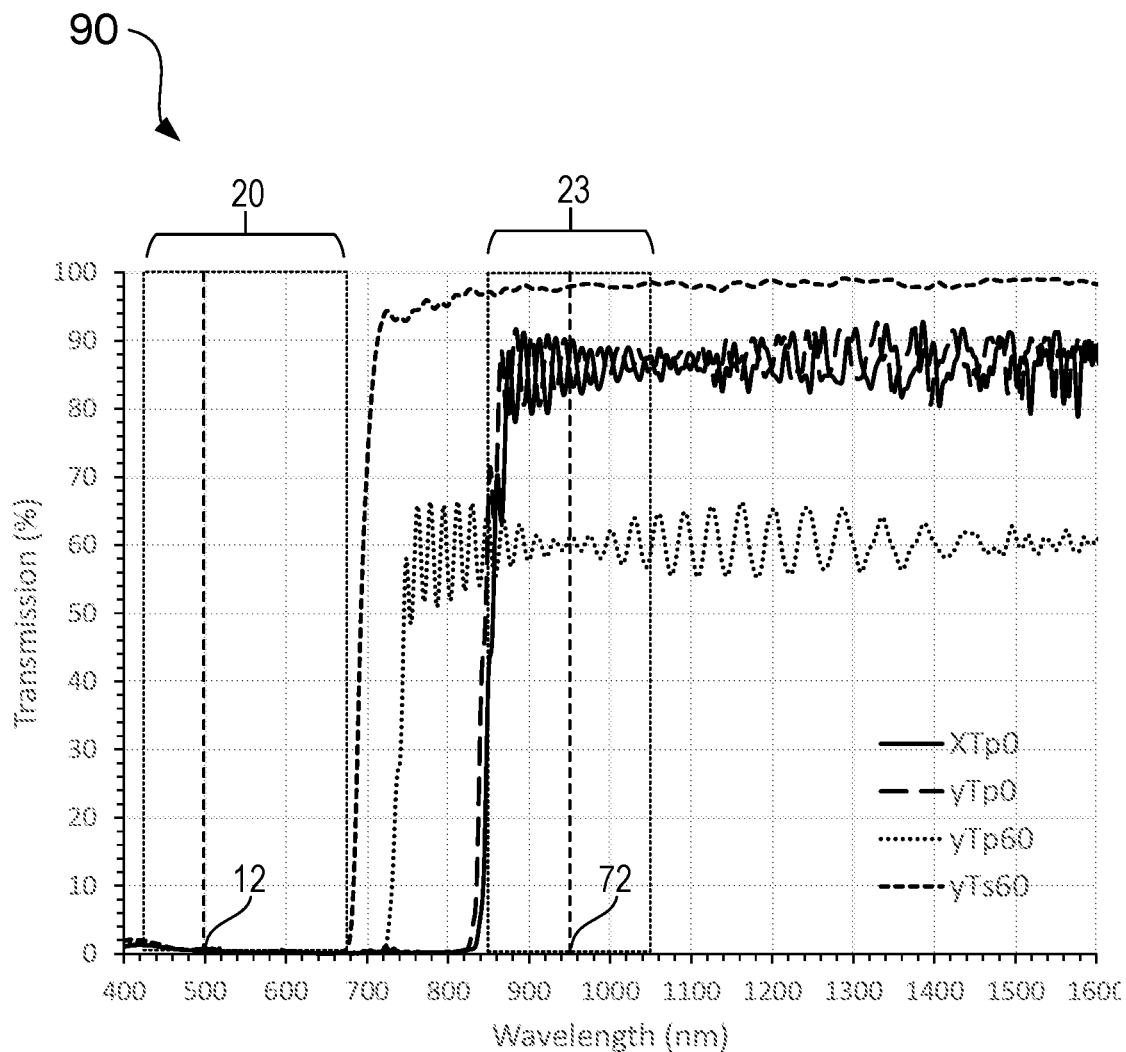
FIGS. 4A and 4B show the transmission percentage versus wavelength characteristics for an optical film which reflects at least some visible wavelengths and substantially transmits at least some infrared wavelengths, in accordance with an embodiment of the present description.

FIGS. 4A and 4B show the transmission percentage versus wavelength characteristics for an optical film which reflects at least some visible wavelengths and substantially transmits at least some infrared wavelengths, such as first optical film 90 of FIG. 1. As shown in the plots of FIG. 4A, first film 90 substantially reflects light (of both polarization types and for incidence angles of both 0 and 60 degrees) in the visible wavelength range 20 (e.g., first wavelength 12). Also, first film 90 allows for substantial transmission of at least some wavelengths in infrared wavelength range 23, such as second wavelength 72, for these same plotlines. The table of FIG. 4B summarizes the transmission percentages for the four plotlines for several wavelength ranges. That is, first film 90 may act as a reflector for visible wavelengths of light, while allowing some infrared wavelengths to be at least partially transmitted, allowing the infrared light to reach sensors through the optical stack of display system 200.

Figures 5A, 5B:
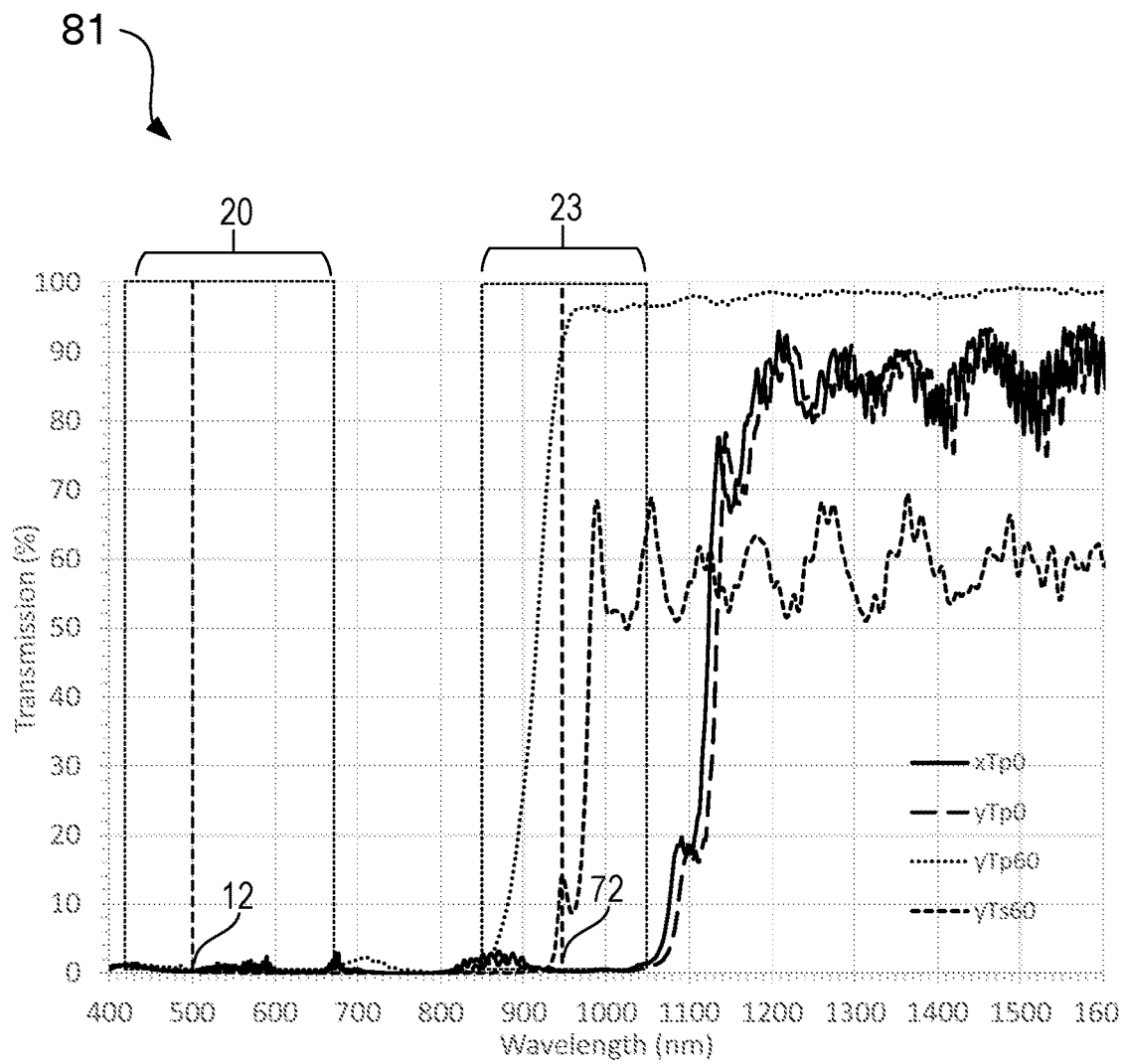
FIGS. 5A and 5B show the transmission percentage versus wavelength characteristics for an optical film which reflects at least some of both visible and infrared wavelengths, in accordance with an embodiment of the present description.

Similarly, FIGS. 5A and 5B show the transmission percentage versus wavelength characteristics for an optical film which reflects at least some of both visible and infrared wavelengths, such as second substrate 81, as shown in FIG. 1. In contrast to the plotlines of reflective polarizer 50 in FIG. 4A, the plotlines for second substrate 81 in FIG. 5A show that the optical film acts substantially as a reflector for both the first wavelength 12 (and visible wavelength range 20) and for second wavelength 72 (and infrared wavelength range 23), especially for normally incident light (i.e., light with an incident angle near 0 degrees) and infrared light in the range of 700 nm to 900 nm at higher angles of incidence (such as at an incidence angle of about 60 degrees). The table of FIG. 5B provides a summary of the average transmission percentages for various wavelength ranges, angles of incidence, and polarization types, based on the plotlines of FIG. 5A.

Figure 6:
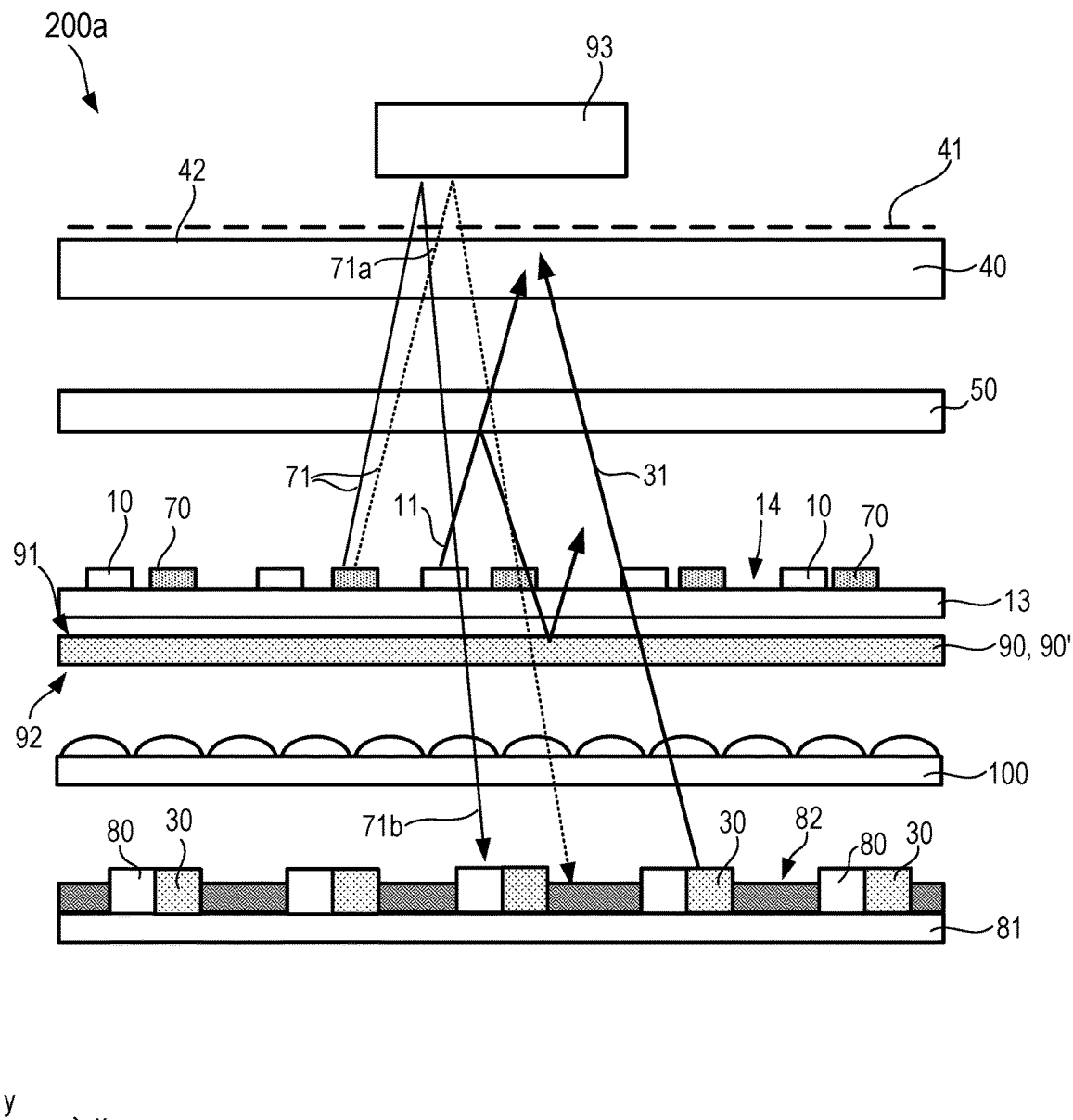
FIG. 6 is a side view of an alternate display system with visible, infrared, and ultraviolet light emitting devices, in accordance with an embodiment of the present description.
Figure 7:
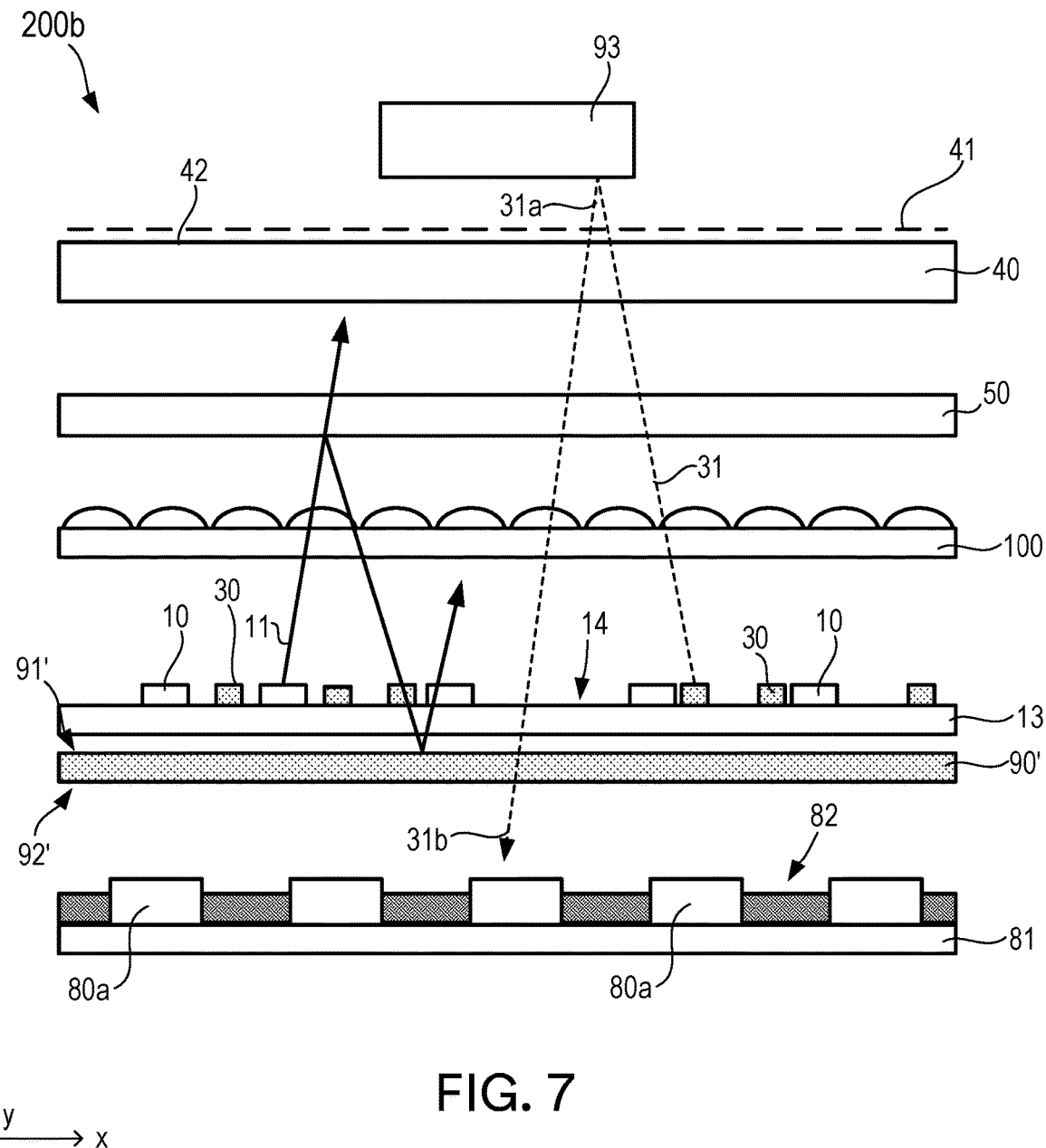
FIG. 7 is a side view of yet another alternate display system with visible, infrared, and ultraviolet light emitting devices, in accordance with an embodiment of the present description.

FIGS. 6 and 7 detail alternate embodiments of a display system, according to the present description. Both of FIGS. 6 and 7 share like-numbered elements with display system 200 of FIG. 1, and these elements shall be assumed to have a similar function as their like-numbered counterparts in FIG. 1 unless specifically noted otherwise. As such, additional description may not be provided for elements in FIGS. 6 and 7 which have already been described in FIG. 1, and the description provided for these elements for FIG. 1 will likewise apply to FIGS. 6 and 7.

In the embodiment of FIG. 6, display system 200a may include one or more visible light emitting first devices 10, one or more infrared light emitting second devices 70, one or more ultraviolet light emitting third devices 30, and one or more infrared light detecting fourth devices 80. In the embodiment of FIG. 6, the first devices 10 and second devices 70 may be disposed on a same common first substrate 13, and third devices 30 and fourth devices 80 may be disposed on a same common second substrate 81. That is, in this embodiment, the ultraviolet emitting third devices 30 and infrared detecting fourth devices 80 are on the same substrate 81 and separated from first devices 10 and second devices 70 by at least optical film 90. (Note: Optical film 90' shown in FIG. 6 is another embodiment of optical film 90 and will be discussed in additional detail elsewhere herein. Either embodiment 90 or 90' may be used in the embodiment of FIG. 6.) That is, first devices 10 and second devices 70 may be disposed on a first side 91 of first film 90 and the third devices 30 and fourth devices 80 may be disposed on an opposite second side 92 of first film 90.

In some embodiments, the one or more visible light emitting first devices 10 may be configured to emit a first light 11 having at least a first wavelength 12 in a visible wavelength range 20 extending from about 425 nm to about 680 nm (see, e.g., wavelength 12 of FIG. 2). In some embodiments, the one or more infrared light emitting second devices 70 may be configured to emit a second light 71 having at least a second wavelength 72 in an infrared wavelength range 23 extending from about 850 nm to about 1050 nm (see, e.g., wavelength 72 of FIG. 2). In some embodiments, the one or more ultraviolet light emitting third devices 30 may be configured to emit a third light 31 having at least a third wavelength 32 in an ultraviolet wavelength range (see, e.g., wavelength 32 of FIG. 2). In some embodiments, the one or more infrared light detecting fourth devices 80 may be configured to detect a fourth light 71b having the at least the second wavelength 72.

In some embodiments, display system 200a may further include a display panel 40 and a reflective polarizer 50 disposed between the display panel and the first devices 10, second devices 70, third devices 30, and fourth devices 80. In some embodiments, display system 200a may further include an optical diffuser 100 disposed between the first optical film 90 and the third devices 30 and configured to diffuse light 31 emitted by the one or more ultraviolet light emitting third devices 30.

Stated another way, some differences between the embodiment 200 of FIG. 1 and embodiment 200a of FIG. 6 include moving the ultraviolet emitting third devices 30 to a common substrate 81 with infrared detecting fourth devices 80 and moving the optical diffuser 100 such that it is disposed directly adjacent third devices 30 such that it diffuses light 31 emitted by third devices 30. In some embodiments, optical film 90 (or 90') may be configured to allow the substantial transmission of ultraviolet light 31. In some embodiments, this light 31 may reach display panel 40 and disinfect at least an exposed front surface 42 of display panel 40.

Although some embodiments described herein rely on the detection of infrared light 71a reflected from an object 93 in order to determine a location of object 93 relative to display panel 40, in other embodiments, the same location determination function may be accomplished with reflected ultraviolet light. FIG. 7 details an embodiment of display system 200b which uses ultraviolet light 31 to detect an object 93 proximate the front surface 42 of display panel 41.

In the embodiment of FIG. 7, display system 200 may include one or more visible light emitting first devices 10, one or more ultraviolet light emitting second devices 30, one or more ultraviolet light detecting third devices 80a, a display panel 40 configured to form an image 41, a reflective polarizer 50 disposed between display panel 40 and the first devices 10, second devices 30, and third devices 80a, and an optical film 90' disposed so that first devices 10 and second devices 30 are on a first side 91' of optical film 90' and third devices 80a are on an opposite second side 92' of the optical film 90'.

In some embodiments, the one or more visible light emitting first devices 10 may be configured to emit a first light 11 having at least a first wavelength 12 in a visible wavelength range 20 extending from about 420 nm to about 680 nm (see FIG. 2A), the one or more ultraviolet light emitting second devices 30 may be configured to emit a second light 31 having at least a second wavelength 32 less than about 415 nm (see FIG. 2A), and the one or more ultraviolet light detecting third devices 80a may be configured to detect a third light 31b having the at least the second wavelength 32.

In some embodiments, for a substantially normally incident light 60 (see e.g., incident light 60, FIG. 3), reflective polarizer 50 may have an average optical reflectance for the visible wavelength range 20 of greater than about 50%, or greater than about 55%, or greater than about 60%, or greater than about 70%, or greater than about 75%, or greater than about 80%, or greater than about 85%, or greater than about 90% when the incident light is polarized along an in-plane first direction (e.g., along the x-axis, see, e.g., FIG. 2B, Rx(0) for the range 420 nm-680 nm), an average optical transmittance of greater than about 50%, or greater than about 55%, or greater than about 60%, or greater than about 65%, or greater than about 70%, or greater than about 75% when the incident light is polarized along an in-plane orthogonal second direction (e.g., along the y-axis, see, e.g., Ty(0), FIG. 2B, for 420 nm-680 nm), and an optical transmission of greater than about 30%, or greater than about 35%, or greater than about 40%, or greater than about 45%, or greater than about 50%, or greater than about 55%, or greater than about 60%, or greater than about 65%, or greater than about 70%, or greater than about 75%, or greater than about 80% for the at least the second wavelength and for at least one of the first and second polarization states (see, e.g., FIG. 2B, Tx(0) and Ty(0) for wavelength 390 nm).

In some embodiments, for each of the incident light polarized along the in-plane first and second directions, the optical film 90' may have an average optical reflectance of greater than about 60%, or greater than about 65%, or greater than about 70%, or greater than about 75%, or greater than about 80%, or greater than about 85%, or greater than about 90%, or greater than about 95%, or greater than about 98% for the visible wavelength range 20 and an optical transmittance of greater than about 50%, or greater than about 55%, or greater than about 60%, or greater than about 65%, or greater than about 70% for the at least the second wavelength 32. Additional details about optical film 90' can be found in FIGS. 9A-9C elsewhere herein.

In the embodiment of FIG. 7, ultraviolet light 31 is emitted by second devices 30. Ultraviolet light 31 is reflected by an object 93 (e.g., a finger or stylus) near front surface 42 of display panel 40 and reflected as reflected ultraviolet light 31a. Reflected ultraviolet light 31a passes through display system 200 and is detected as received ultraviolet light 31b by third devices 80a. This received ultraviolet light 31b may be used to determine a position of object 93 in relation to front surface 42.

Figure 8:
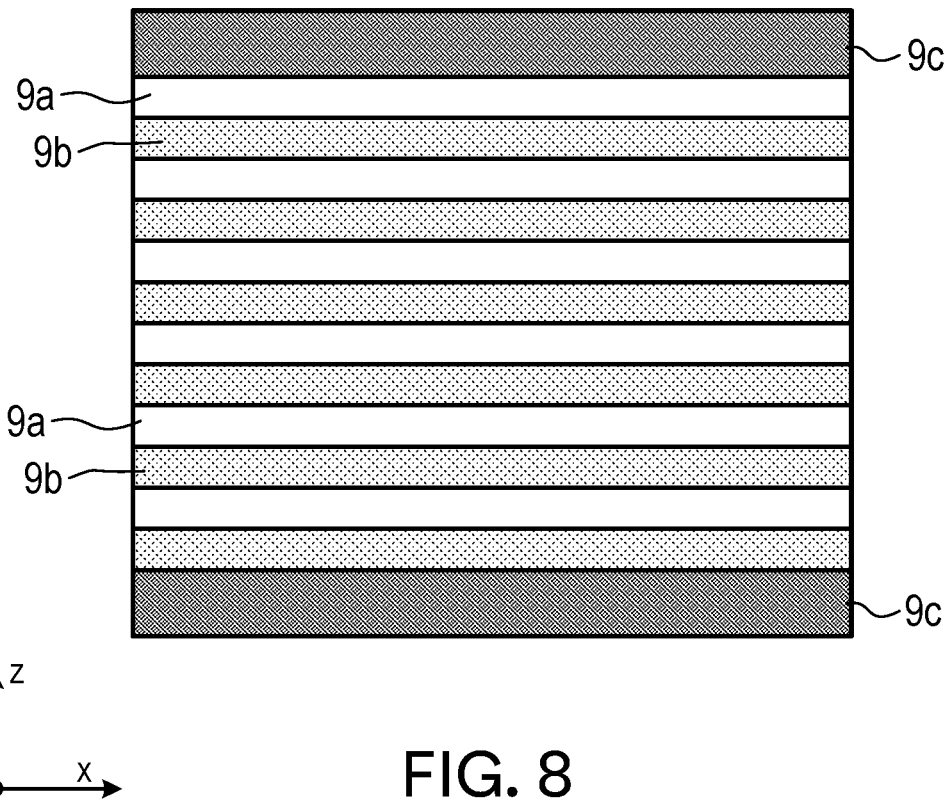
FIG. 8 is an illustration of the layered architecture of a multilayer optical film, in accordance with an embodiment of the present description.

FIG. 8 is an illustration of an embodiments of a layered architecture which may be exhibited by any of the multilayer optical films discussed herein, including the reflective polarizer 50 of FIG. 1 (and other figures), optical film 90 of FIG. 1 (and other figures), optical film 90' of FIG. 1 (and other figures), and optical films 94, 95, and 96, which will be discussed in the description of FIGS. 9A-9C. In some embodiments, and of these films may be a multilayer optical film having a plurality of alternating polymeric layers 9a and 9b numbering at least 10, or at least 50, or at least 100, or at least 150, or at least 200, or at least 250, or at least 300 in total. In some embodiments, each of the polymeric layers 9a and 9b may have an average thickness of less than about 500 nm, or less than about 450 nm, or less than about 400 nm, or less than about 350 nm, or less than about 300 nm, or less than about 250 nm, or less than about 200 nm. In some embodiments, the multilayer optical films may further include one or more outer skin layers 9c. By configuring the indices of refraction of alternating layers 9a and 9b, a multilayer film may be configured to match any of the optical transmission plots provided herein, including the plots of FIGS. 2A, 4A, 5A, and 9A herein.

Figure 9A:
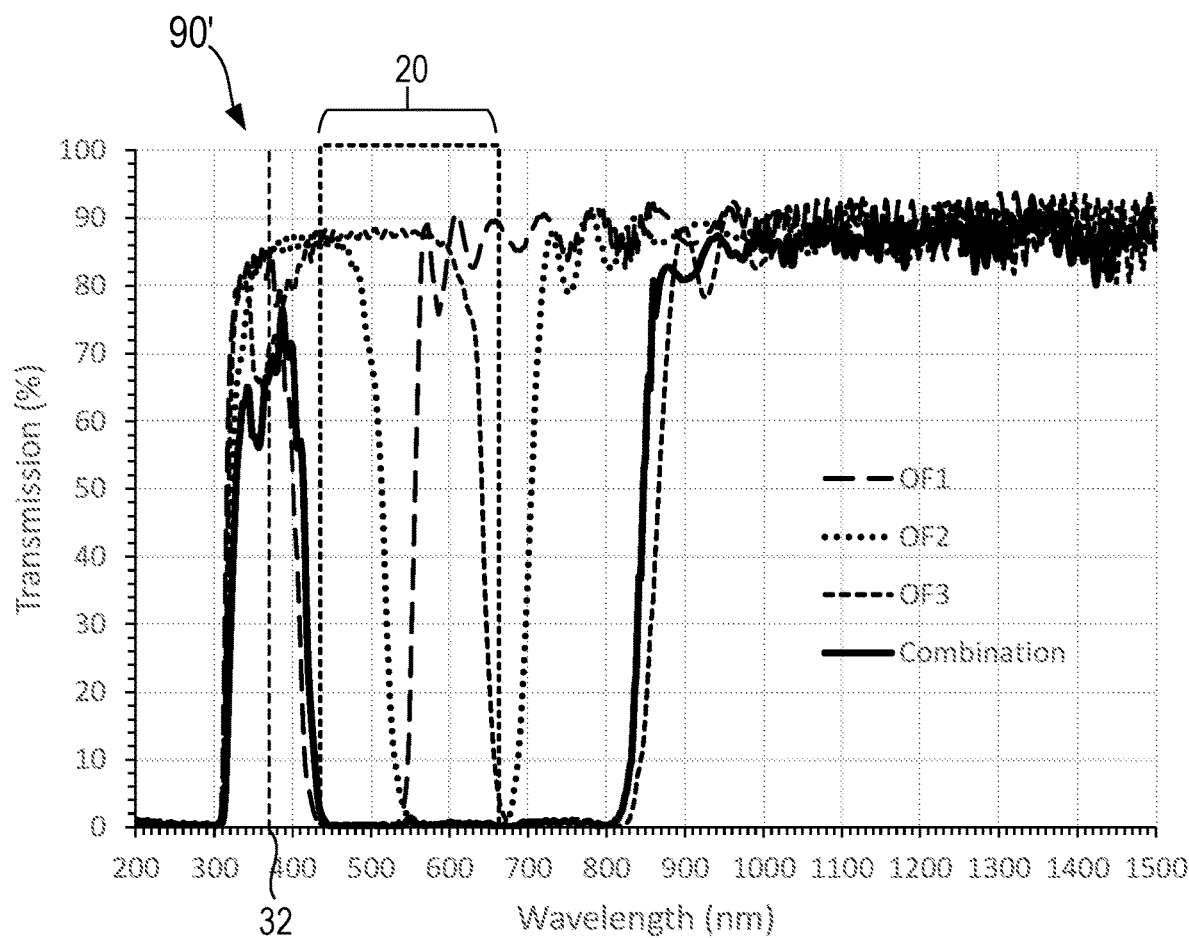
Figure 9B:
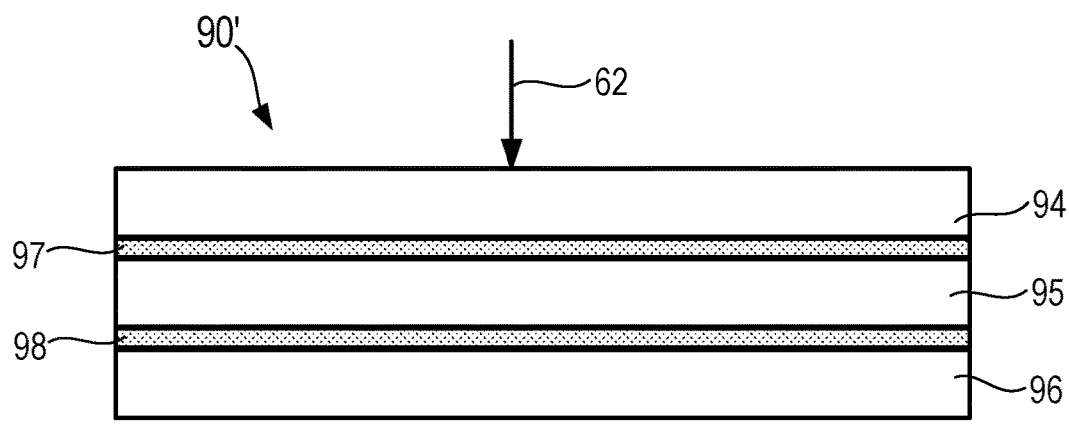

Finally, FIGS. 9A-9C is a chart showing the transmission percentage versus wavelength for an optical film 90' such as that shown in FIGS. 1, 6, and 7. Turning first to FIG. 9B, optical film 90' may, in some embodiments, include a first optical film 94, a second optical film 95, and a third optical film 96 (Note: first optical film 94, a second optical film 95, and a third optical film 96 may be thought of as layers or sub-films of optical film 90'). In some embodiments, the first optical film 94, a second optical film 95, and a third optical film 96 may be bonded to each other via a first adhesive layer 97 and a second adhesive layer 98.

Combining the individual optical characteristic of first optical film 94, a second optical film 95, and a third optical film 96 (shown respectively as OF1, OF2, and OF3 in the plot of FIG. 9A), a "combination" film 90' may be configured that has optical characteristics similar to those shown in FIG. 9A. Looking at the "combination" plotline of FIG. 9A (the solid dark line), optical film 90' exhibits a high optical reflectance in the visible wavelength range 20, and a relatively high optical transmission for ultraviolet wavelength 32. FIG. 9C provides a summary in the form of tables which illustrates the transmission and reflection percentages for various wavelengths and wavelength ranges for each sub-film (OF1, OF2, OF3) and for the combination film 90'.

Terms such as "about" will be understood in the context in which they are used and described in the present description by one of ordinary skill in the art. If the use of "about" as applied to quantities expressing feature sizes, amounts, and physical properties is not otherwise clear to one of ordinary skill in the art in the context in which it is used and described in the present description, "about" will be understood to mean within 10 percent of the specified value. A quantity given as about a specified value can be precisely the specified value. For example, if it is not otherwise clear to one of ordinary skill in the art in the context in which it is used and described in the present description, a quantity having a value of about 1, means that the quantity has a value between 0.9 and 1.1, and that the value could be 1.

Terms such as "substantially" will be understood in the context in which they are used and described in the present description by one of ordinary skill in the art. If the use of "substantially equal" is not otherwise clear to one of ordinary skill in the art in the context in which it is used and described in the present description, "substantially equal" will mean about equal where about is as described above. If the use of "substantially parallel" is not otherwise clear to one of ordinary skill in the art in the context in which it is used and described in the present description, "substantially parallel" will mean within 30 degrees of parallel. Directions or surfaces described as substantially parallel to one another may, in some embodiments, be within 20 degrees, or within 10 degrees of parallel, or may be parallel or nominally parallel. If the use of "substantially aligned" is not otherwise clear to one of ordinary skill in the art in the context in which it is used and described in the present description, "substantially aligned" will mean aligned to within 20% of a width of the objects being aligned. Objects described as substantially aligned may, in some embodiments, be aligned to within 10% or to within 5% of a width of the objects being aligned.

All references, patents, and patent applications referenced in the foregoing are hereby incorporated herein by reference in their entirety in a consistent manner. In the event of inconsistencies or contradictions between portions of the incorporated references and this application, the information in the preceding description shall control.

Descriptions for elements in figures should be understood to apply equally to corresponding elements in other figures, unless indicated otherwise. Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed:

1. A display system comprising:
   one or more visible light emitting first devices configured to emit a first light having at least a first wavelength in a visible wavelength range extending from about 425 nm to about 680 nm;
   one or more ultraviolet light emitting second devices configured to emit a second light having at least a second wavelength less than about 425 nm;
   a display panel disposed on the first and second devices and configured to receive the emitted first and second lights and form an image; and
   a reflective polarizer disposed between the display panel and the first and second devices, such that for a substantially normally incident light, the reflective polarizer has:
   for the visible wavelength range, an average optical reflectance of greater than about 50% when the incident light is polarized along an in-plane first direction and an average optical transmittance of greater than about 50% when the incident light is polarized along an in-plane orthogonal second direction; and
   an optical transmission of greater than about 30% for the at least the second wavelength and for at least one of the first and second polarization states.

2. The display system of claim 1, wherein the second light is configured to reach and disinfect at least an exposed front surface of the display system.

3. The display system of claim 1 further comprising:
   one or more infrared light emitting third devices configured to emit a third light having at least a third wavelength in an infrared wavelength range extending from about 850 nm to about 1050 nm;
   one or more infrared light detecting fourth devices configured to detect a fourth light having the at least the third wavelength; and
   an optically reflecting first film disposed between the third and the fourth devices, such that for a substantially normally incident light and for each of the incident light polarized along the in-plane first and second directions, the optically reflecting first film has an average optical reflectance of greater than about 60% for the visible wavelength range and an average optical transmittance of greater than about 50% for the infrared wavelength range.

4. The display system of claim 3, wherein the first, second and third devices are disposed on a same common first substrate, and wherein at least in regions between the first, second, and third devices and for a substantially normally incident light and for each of the first and second polarization states, the first substrate has an optical transmittance of greater than about 60% for each of the at least the first and the third wavelengths.

5. The display system of claim 3, wherein the fourth devices are disposed on a same common second substrate, and wherein at least in regions between the fourth devices and for a substantially normally incident light and for each of the first and second polarization states, the second substrate has an optical absorption of greater than about 60% at the at least the third wavelength.

6. The display system of claim 3 configured so that an object disposed proximate the display system reflects at least a portions of the third light toward the fourth devices as a third reflected light, the optically reflecting first film configured to transmit at least 30% of the third reflected light as a third transmitted light, each of at least three of the fourth devices configured to receive and detect at least 5% of the third transmitted light, the detection by the at least three of the fourth devices, in combination, allowing a detection of a location of the object.

7. The display system of claim 1, wherein the first and second devices are disposed on a same common first substrate, and wherein at least in regions between the first and second devices and for a substantially normally incident light and for each of the first and second polarization states, the first substrate has an optical transmittance of greater than about 60% for the at least the first wavelength.

8. The display system of claim 1 further comprising an optical diffuser disposed between the reflective polarizer and the second devices and configured to diffuse the second light emitted by the one or more ultraviolet light emitting second devices.

9. A display system comprising:
   one or more visible light emitting first devices configured to emit a first light having at least a first wavelength in a visible wavelength range extending from about 425 nm to about 680 nm;
   one or more infrared light emitting second devices configured to emit a second light having at least a second wavelength in an infrared wavelength range extending from about 850 nm to about 1050 nm;
   one or more ultraviolet light emitting third devices configured to emit a third light having at least a third wavelength less than about 425 nm;
   one or more infrared light detecting fourth devices configured to detect a fourth light having the at least the second wavelength;

a display panel disposed on the first through fourth devices and configured to receive at least the emitted first and third lights and form an image;

a reflective polarizer disposed between the display panel and the first through fourth devices; and an optically reflecting first film disposed so that the first and the second devices are on a first side of the optically reflecting first film and the third and the fourth devices are on an opposite second side of the optically reflecting first film, such that for a substantially normally incident light, the reflective polarizer has:

for the visible wavelength range, an average optical reflectance of greater than about 50% when the incident light is polarized along an in-plane first direction and an average optical transmittance of greater than about 50% when the incident light is polarized along an in-plane orthogonal second direction; and an optical transmission of greater than about 30% for the at least the third wavelength and for at least one of the first and second polarization states; and for each of the incident light polarized along the in-plane first and second directions, the optically reflecting first film has an average optical reflectance of greater than about 60% for the visible wavelength range and an average optical transmittance of greater than about 50% for the infrared wavelength range.

10. The display system of claim 9 configured so that an object disposed proximate the display system reflects at least a portions of the second light toward the fourth devices as a second reflected light, the optically reflecting first film configured to transmit at least 30% of the second reflected light as a second transmitted light, each of at least three of the fourth devices configured to receive and detect at least 5% of the second transmitted light, the detection by the at least three of the fourth devices, in combination, allowing a detection of a location of the object.

11. The display system of claim 9, wherein for the substantially normally incident light and for each of the incident light polarized along the in-plane first and second directions, the optically reflecting first film has an optical transmission of greater than about 30% for the at least the third wavelength.

12. The display system of claim 9, wherein the fourth light is configured to reach and disinfect at least an exposed front surface of the display system.

13. A display system comprising:
one or more visible light emitting first devices configured to emit a first light having at least a first wavelength in a visible wavelength range extending from about 420 nm to about 680 nm;

one or more ultraviolet light emitting second devices configured to emit a second light having at least a second wavelength less than about 415 nm;

one or more ultraviolet light detecting third devices configured to detect a third light having the at least the second wavelength;

a display panel disposed on the first through third devices and configured to receive at least the emitted first and second lights and form an image;

a reflective polarizer disposed between the display panel and the first through third devices; and an optical film disposed so that the first and the second devices are on a first side of the optical film and the third devices are on an opposite second side of the optical film, such that for a substantially normally incident light, the reflective polarizer has:

for the visible wavelength range, an average optical reflectance of greater than about 50% when the incident light is polarized along an in-plane first direction and an average optical transmittance of greater than about 50% when the incident light is polarized along an in-plane orthogonal second direction; and an optical transmission of greater than about 30% for the at least the second wavelength and for at least one of the first and second polarization states; and for each of the incident light polarized along the in-plane first and second directions, the optical film has an average optical reflectance of greater than about 60% for the visible wavelength range and an optical transmittance of greater than about 50% for the at least the second wavelength.

14. The display system of claim 13, wherein the optical film comprises first, second, and third optical films, each of the first, second and third optical films comprising a plurality of polymeric layers numbering at least 10 in total, each of the polymeric layers having an average thickness of less than about 500 nm, such that for a substantially normally incident light, three spaced apart wavelengths in a reflection wavelength range extending from about 450 nm to about 800 nm, and for each of the incident light polarized along the in-plane first and second directions, each of the first, second and third optical films has:

an optical transmittance of greater than about 50% for the at least the second wavelength; and has an optical transmittance T1 for one of the three spaced apart wavelengths and an optical transmittance T2 for each of the other two of the three spaced apart wavelengths, T2/T1≥10.

15. The display system of claim 13, wherein the first, second, and third optical films are bonded to each other via first and second adhesive layers.

16. The display system of claim 13, wherein the third light is configured to reach and disinfect at least an exposed front surface of the display system.

* * * * *